United States Patent [19]

Sauerwein et al.

[11] Patent Number: 4,692,628
[45] Date of Patent: Sep. 8, 1987

[54] PIPELINE SWITCH

[75] Inventors: Kurt Sauerwein, Kattendahl 7, 4006 Erkrath 2; Norbert Kinzer, Wuppertal, both of Fed. Rep. of Germany; Felix W. Mick, Bronx, N.Y.

[73] Assignee: Kurt Sauerwein, Erkrath, Fed. Rep. of Germany

[21] Appl. No.: 798,158

[22] Filed: Oct. 30, 1985

Related U.S. Application Data

[63] Continuation of Ser. No. 532,580, Sep. 15, 1983, abandoned.

[30] Foreign Application Priority Data

Apr. 16, 1983 [DE] Fed. Rep. of Germany ....... 3313857

[51] Int. Cl.$^4$ .............................................. G21F 5/02
[52] U.S. Cl. .............................. 250/497.1; 250/496.1; 406/182
[58] Field of Search ................... 200/5 R, 50 R, 50 C, 200/11 R, 52 R, 153 S; 250/491.1, 492.1–498.1, 503.1, 432 R, 432 PD, 364; 378/193, 195, 196, 203, 64, 68; 406/182

[56] References Cited

U.S. PATENT DOCUMENTS

| 2,629,048 | 2/1953 | Dyke et al. | 200/153 S X |
| 2,709,725 | 5/1955 | Bieber et al. | 200/153 S |
| 2,816,198 | 12/1957 | Cherry | 200/153 S |
| 2,825,604 | 3/1958 | Sebestyen | 406/182 |
| 3,369,096 | 2/1968 | Gattaz | 200/153 S |
| 3,669,093 | 6/1972 | Sauerwein et al. | 250/497.1 X |
| 4,150,298 | 4/1979 | Brault et al. | 250/497.1 |
| 4,206,332 | 6/1980 | Veenendual | 200/153 S |
| 4,220,864 | 9/1980 | Sauerwein et al. | 250/497.1 |

FOREIGN PATENT DOCUMENTS

| 1456761 | 1/1970 | Fed. Rep. of Germany . |
| 1781388 | 9/1972 | Fed. Rep. of Germany . |
| 43360 | 8/1968 | German Democratic Rep. | 406/182 |
| 733013 | 7/1955 | United Kingdom | 406/182 |

Primary Examiner—J. R. Scott
Attorney, Agent, or Firm—Toren, McGeady & Associates

[57] ABSTRACT

A pipeline switch for selectively connecting a loading pipe to one of several secondary pipes or conduits includes an apertured plate with several through-holes for rigid connection in alignment with the secondary pipes or conduits, a pipe plate rotatable parallel to the apertured plate and having a through-hole which can be aligned with any one of the through-holes of the apertured plate and with which the loading pipe is rigidly connected in alignment, and a control unit for rotating and locking the apertured plate in relation to the pipe plate. A radiation source can be guided by a cable through the loading pipe into the aligned one of the secondary pipes.

5 Claims, 3 Drawing Figures

PIPELINE SWITCH

This is a continuation of application Ser. No. 532,580, filed Sept. 15, 1983, now abandoned.

BACKGROUND OF THE INVENTION

The invention concerns a pipeline or duct switch for selectively connecting a loading conduit to one of several secondary conduits.

Such conduits may be plastics or flexible metal hoses which provide external protection and a guide for a cable in the form of a flexible wire axially movable within the conduit. A switch of this kind is required for precise mutual positioning of the conduits to be connected end to end, i.e. high-precision alignment, rather than sealing tightness of the connection, which is of secondary importance. Medical and radiation technology is a typical field of application of such a switch; for in these fields, radiation sources have frequently to be guided to a particular location with high accuracy. In the context of radiation technology it must constantly be ensured that a radiation source is not damaged in a conduit or even comes out of a conduit into an unprotected environment. This risk is present above all when several conduits to be connected to a single conduit can be selectively coupled to the pipeline switch and uncoupled from it.

The distribution of rays obtainable at the object of irradiation, e.g. in interstitial or intracavity tumor therapy, only covers a region of volume which is defined by the length of the hollow probe and the depth of penetration of radiation, and which consequently has essentially a linear dimension. Three-dimensional distribution of radiation can therefore be obtained only with several radiation sources. In addition, so-called afterloading devices may have available to them several pipes, radiation sources, radiation shielding bodies and applicators, or after each irradiation process in an applicator the connecting hose must be uncoupled from the afterloading device and the connecting hose of the next applicator coupled on.

Multi-pipe devices are, for technical reasons, limited to three or six pipes and, according to the number of pipes, very expensive. They cannot likewise be operated fully automatically for applications with more than six applicators, such as e.g. in the case of irridation of neck tumors and breast cancer, if the number of applicators required exceeds the number of pipes. Changing the hoses from applicator to applicator each time with a single-pipe device is, on the other hand, very time-consuming and inconveniences the patient.

SUMMARY OF THE INVENTION

The invention is therefore based on the object of providing, in a pipeline switch of the aforementioned kind, an automatic control which permits very precise alignment as well as automatic control of accuracy and precision of the respective conduit connection. Furthermore, it is intended to make it possible, in a simple manner, to prevent use of a connection when a conduit is not connected, or not correctly connected at its free end to a secondary circuit. In particular, a simple and efficient pipeline switch for afterloading devices is desired.

This object is achieved in a pipeline switch for selectively connecting a loading conduit or pipe to one of several secondary conduits or pipes, characterised by a first plate with several through-holes adapted for rigid connection in use in alignment with the ends of respective ones of said secondary conduits; a second plate rotatable parallel to said first plate and having a through-hole, which can be aligned with a selected one of said through-holes of said first plate, and with which said loading conduit is rigidly connected in alignment; and control means for rotating and locking said second plate relatively to said first plate. The pipline switch connects the loading pipe to one of the secondary pipes so that a source capsule, such as a radiation source capsule, can be moved through the loading pipe and into a selected one of the secondary pipes.

In this way, the loading pipe or other conduit is rapidly, reliably and automatically coupled to a predetermined secondary conduit, but also controlled at its end adjacent to the pipeline switch. Hence there is provided, above all for afterloading devices in which the loading pipe makes a connection to the radiation-shielding body and the secondary pipes or conduits act as connections to the individual applicators, an extraordinarily simple, cheap and reliable option of making a multi-pipe device which is easy to operate out of a relatively inexpensive single-pipe device. Thus, even existing single-pipe devices can subsequently be equipped with the pipeline switch.

A pipe switch according to the invention can be particularly easily manipulated if the first plate is stationary and fitted with a locking unit as well as a drive motor for rotating the pipe plate. Particularly suitable as a locking unit is an electromagnet of which the core carries a pin which engages in recesses arranged concentrically about the axis of rotation of the rotatable second plate when whichever connection desired is in exact alignment. These recesses may be arranged radially or axially on the rotatable plate, and provided with a concentrically outwardly diverging centering opening for the locking pin which preferably also tapers conically for centering purposes.

A potentiometer movable by the rotatable second plate allows accuracy of the pipeline switch position to be monitored. For this, the movable shaft of a rotary potentiometer may be actuated by the rotatable plate by means of a concentric connection. Above all, a rack and pinion drive or belt drive engaging the second plate laterally is suitable as the drive for the rotatable plate. By this means, when the rotary switch is accommodated in a cylindrical housing, there is obtained eccentrically of the axis of rotation which can be selected for an afterloading device, as it coincides with the eccentric opening in a front plate of the head of the radiation source. In this way, the leading conduit is subjected to the least stress, and easy connection of the head of the radiation source to the switch is obtained.

Accidental use of a conduit can be avoided by a safety limit switch controlling the through-holes of the first and/or second plate.

BRIEF DESCRIPTION OF THE DRAWING

The invention is explained in more detail below with the aid of an example shown in the drawings. In the drawings.

DETAILED DESCRIPTION OF THE INVENTION

Figure 1:
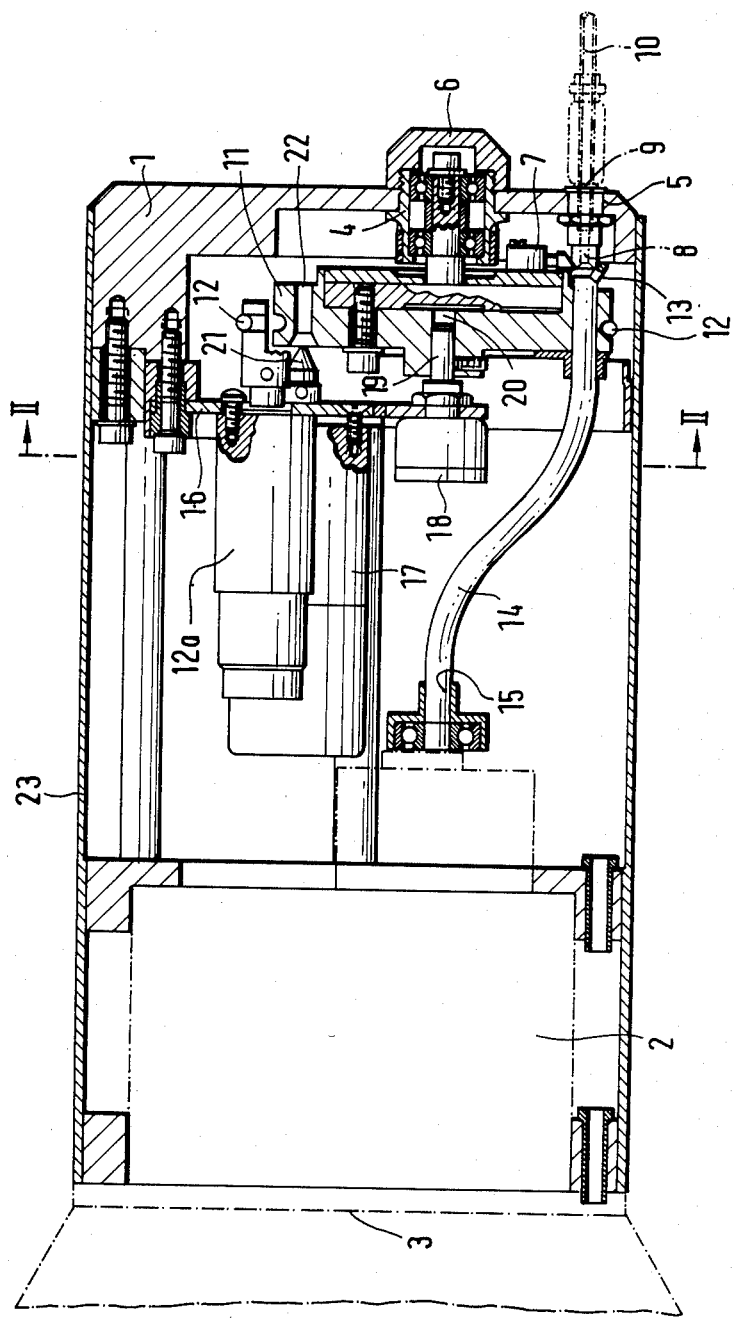
FIG. 1 shows a pipe switch at the head of the radiation source of an afterloading device in partial axial section.
Figure 2:
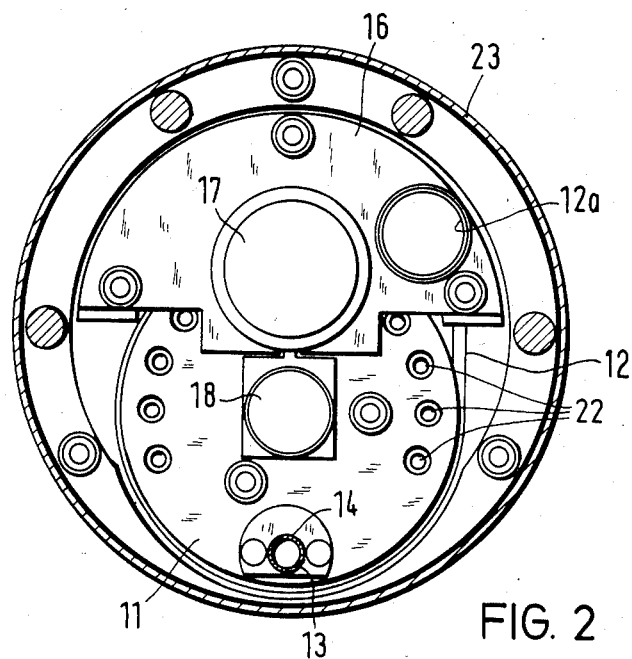
FIG. 2 is a section taken on the line II—II in FIG. 1.
Figure 3:
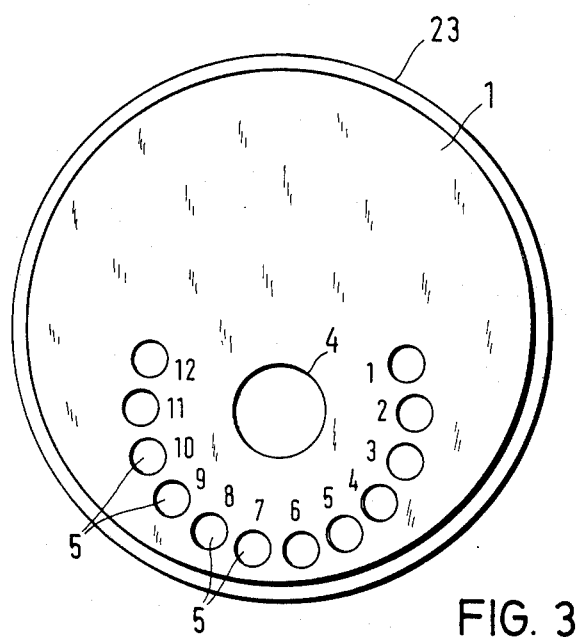
FIG. 3 is a front elevation of the pipe switch.

A stationary apertured plate 1 forms the end face of a cylindrical housing 23 coaxially connected to a radiation source head 2 of an afterloading device 3 otherwise not shown in more detail. The apertured plate 1 comprises an eccentric bearing or support hole 4 for a pivot bearing and, coaxial with this hole, twelve conduit holes 5 arranged roughly in a semicircle. By means of a screw cap 6, the pivot bearing hole 4 is closed. Hollow plug-in connectors 9 can be inserted in the conduit holes 5 to form connections to secondary pipes or conduits 10 leading away from the apertured plate 1. The front end 8 of a plug-in connector 9, when this is inserted properly, actuates a safety limit switch 7 on a pipe plate 11, which then releases the drive for a cable which is guided in the conduit and not shown specially in the drawings.

The pipe plate 11 is mounted freely rotatably in the pivot bearing hole or support 4 in the stationary apertured plate 1, and can be displaced electromechanically by means of a belt drive 12 driven by a drive motor 12a. The plate 11 comprises a loading pipe conduit hole 13 to be aligned with any one of the conduit holes 5 in the stationary apertured plate 1 and having a connected loading pipe 14 which is rigidly connected at its other end to an orifice 15 in the head 2, concentrically with the pivot bearing hole 4.

A carrier plate 16 rigidly connected to the stationary plate 1 holds the motor of the belt drive 12, an electromagnet 17 and a rotary potentiometer 18, and can be brought into exact alignment with the rotatable plate 11. The rotary shaft 19 of the rotary potentiometer 18 engages in a central hole 20 in the pipe plate 11 and is held there by a clamping effect and displaced with it synchronously, while the potentiometer housing is secured by the carrier plate 16 and connected in conventional manner by electrical contacts to a control unit not shown in the drawings.

The electromagnet 17 comprises at its end face an axially movable locking pin 21 which, after precise adjustment of the carrier plate 16, can engage in recesses 22 which are arranged in the pipe plate 11 concentrically to the pivot bearing hole 4 and which diverge conically towards the locking pin 21, with the cone angle corresponding roughly to a conical taper at the free end of the locking pin 21. The recesses 22 correspond, with regard to their number and angular spacing, to the conduit holes 5 in the stationary apertured plate 1. When the locking pin 21 is in the recess 22, the pipe hole 13 in the rotatable pipe plate 11 is precisely aligned with one of the conduit holes 5 in the stationary plate 1, this being effected by a single adjustment of the carrier plate 16.

The cylindrical housing 23 connects the stationary apertured plate 1 to the head 2 of the radiation source and hence it supports and protects all the components of the pipeline switch.

The pipeline switch receives its commands from a programmable control unit which, according to a given time program, not only ensures that a radiation source capsule, disposed with radiation shielding in the afterloading device 3, is guided by means of a cable through the loading pipe 14 and by means of the pipeline switch into one of the connected secondary conduits 10 to an applicator, not shown, but also controls the pipeline switch which, in the inoperative position of the radiation source capsule within the afterloading device, may be unlocked, turned to a different connecting position and locked again. Electrical commands ensure that these steps can be carried out only in sequence. The safety limit switch 7 prevents the drive from being able to move the radiation source capsule out of its inoperative position when the loading pipe 14 is not aligned with one of the conduit holes 5 and no conduit 10 is connected to it.

We claim:

1. A pipeline switch apparatus for use in a radiation transfer environment including a radiation shielded afterbody device for holding a radiation source capsule located within said afterbody device in readiness for use, a radiation source head connected to said afterbody device, a loading pipe connected at one end to said head, a cable connected to said radiation source capsule for guiding the capsule from said afterbody device through said head into said loading pipe, a plurality of secondary pipes spaced from said loading pipe and arranged so that a selected one of said secondary pipes can receive said radiation source capsule, wherein the improvement comprises a housing enclosing said radiation source head and said loading pipe, a first plate rigidly secured to said housing and located between said loading pipe and said secondary pipes, said first plate having a plurality of spaced through-holes therethrough each arranged to be aligned with a different one of said secondary pipes, means for interconnecting said through-holes and said secondary pipes, said interconnecting means comprises hollow plug-connectors mounted in said through-holes in said first plate and engaged with said secondary pipes, said through-holes being centered about and spaced radially outwardly from an axis extending perpendicularly through said first plate, a second plate located within said housing between said afterbody device and said first plate and disposed parallel to said first plate and being rotatable about an axis coaxial with the axis through said first plate about which said through-holes are centered, said loading pipe is secured rigidly at the other end thereof in a loading pipe conduit hole in said second plate so that said loading pipe rotates with said second plate for alignment with said interconnecting means and a selected one of said through-holes in said first plate, recesses formed in said second plate and arranged concentrically about the axis of said second plate, drive means for rotating said second plate around the axis thereof, said drive means arranged for rotating said second plate relative to said first plate for interconnecting said loading pipe to one of said secondary pipes whereby a radiation source capsule can be introduced from said afterbody device through said radiation source head and said loading pipe and then through one of said plug-in connectors into one of said secondary pipes, safety switching means actuable by said interconnecting means so that without actuation said safety switching means prevents the displacement of said radiation source capsule from said afterbody device through said second plate when said loading pipe is not aligned with one of said through-holes in said plate, and locking means engageable with said second plate for securing said second plate against rotation when said loading pipe is aligned with one of said through holes in said first plate.

2. A pipeline switch according to claim 1, wherein said first plate is connected stationarily to said locking means, and said drive means comprises a drive motor located within said housing for rotating said second plate, and said first plate is connected to said drive motor.

3. A pipeline switch according to claim 1 wherein said locking means comprises an axially displaceable locking pin engageable in a selected one of said recesses, and means in said housing for axially displacing said locking pin.

4. A pipeline switch according to claim 1 wherein a rotary potentiometer is mounted in said housing and includes a rotary shaft engageable in a central hole in said second plate.

5. A pipeline switch according to claim 1 wherein said safety switching means comprises a spring-loaded safety limit switch engageable with one of said plug-in connectors when one of said through-holes is axially aligned with said loading pipe.

* * * * *

UNITED STATES PATENT AND TRADEMARK OFFICE
CERTIFICATE OF CORRECTION

PATENT NO. : 4,692,628

DATED : September 8, 1987

INVENTOR(S) : Kurt Sauerwein et al

It is certified that error appears in the above-identified patent and that said Letters Patent is hereby corrected as shown below:

On the Title Page:

In the heading of the Patent, it should read:

--[73]  Assignee:  Dr. Kurt Sauerwein

Signed and Sealed this

Twenty-second Day of March, 1988

Attest:

DONALD J. QUIGG

*Attesting Officer*  *Commissioner of Patents and Trademarks*